United States Patent [19]

Hilton et al.

[11] 4,320,658
[45] Mar. 23, 1982

[54] WEIGHING APPARATUS

[75] Inventors: Barney W. Hilton, Dallas; Robert I. Lin, Irving; Greg Crnkovich, Dallas, all of Tex.

[73] Assignee: Frito-Lay, Inc., Dallas, Tex.

[21] Appl. No.: 183,739

[22] Filed: Sep. 3, 1980

[51] Int. Cl.³ .................. G01N 9/10; G01G 19/00; G01G 5/02
[52] U.S. Cl. .................................... 73/437; 177/200; 177/207
[58] Field of Search ................. 177/200, 207; 73/437

[56] References Cited

U.S. PATENT DOCUMENTS

| 1,905,558 | 4/1933  | Foote         |           |
| 2,334,106 | 11/1943 | Lewis         |           |
| 2,704,079 | 3/1955  | Molins et al. |           |
| 2,854,714 | 10/1958 | Dietert       | 177/200 X |
| 3,038,401 | 6/1962  | Bossen        |           |
| 3,246,524 | 4/1966  | Shiba         | 177/207 X |
| 3,351,236 | 11/1967 | Sorenson et al. |         |
| 3,357,341 | 12/1967 | Kocken et al. |           |
| 3,991,619 | 11/1976 | Appleford et al. | 73/437 |

Primary Examiner—George H. Miller, Jr.
Attorney, Agent, or Firm—Bernard, Rothwell & Brown

[57] ABSTRACT

An apparatus suitable for determining the dry and submerged weights of a large volume of water-bearing food material on a more or less continuous basis. The determinations enable the calculation of the density of the food material and, therefore, its solids content.

13 Claims, 2 Drawing Figures

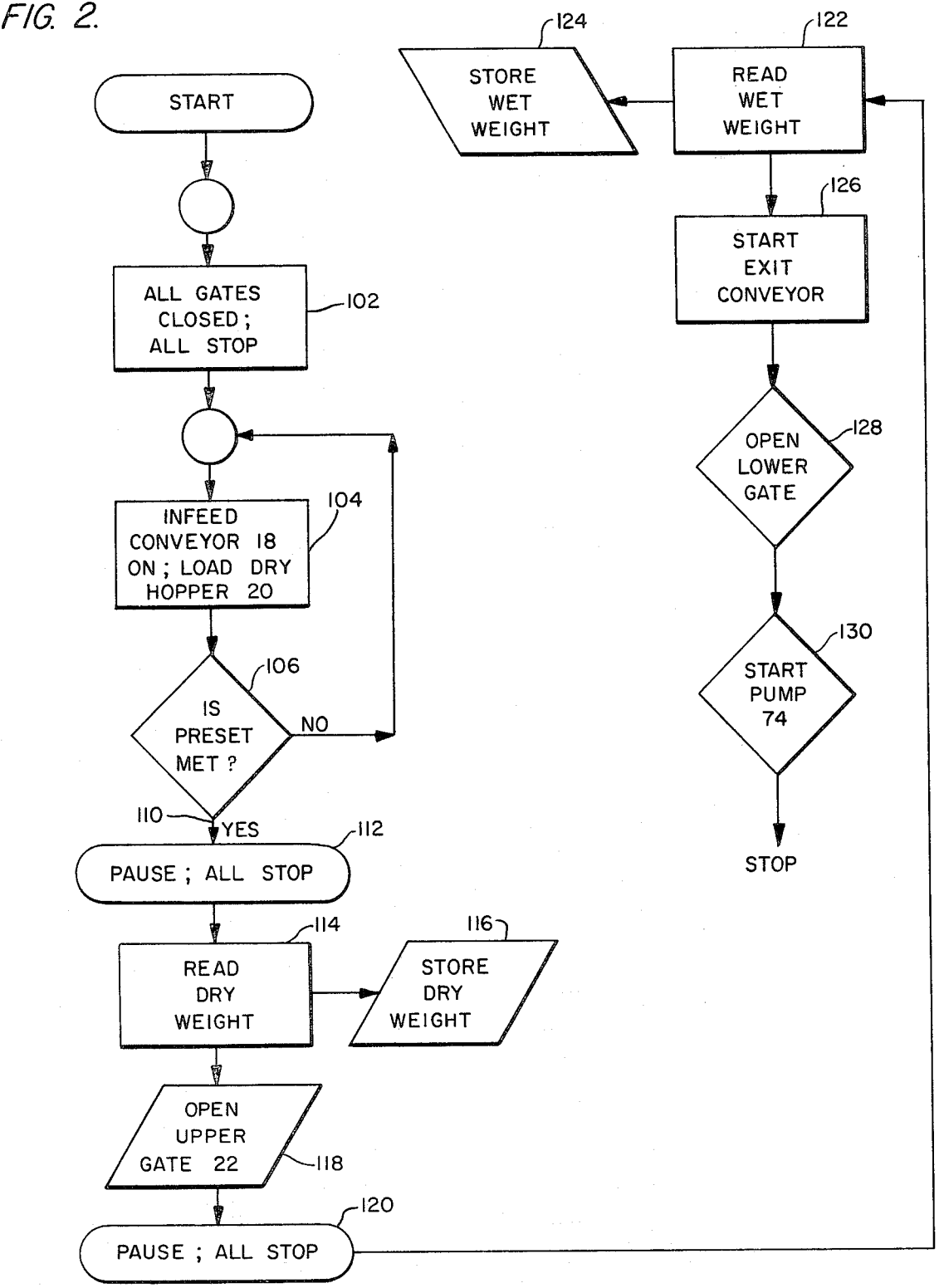

WEIGHING APPARATUS

This invention relates to an apparatus suitable for weighing large volumes of free-flowing, water-bearing food materials in a manner that facilitates the determination of the density and, therefore, the solids content of the materials. The apparatus is particularly adapted for weighing food materials which are to undergo processing for the manufacture of food products, especially processing such as drying, cooking or other treatments in which a major portion of the water content of the material is removed. An example of such manufacture is the production of potato chips from raw potatoes.

In the large scale manufacturing of relatively dry products from food materials containing substantial amounts of water there is a need for determining the density and the solids content of the materials. This information is useful, for example, in establishing and maintaining plant efficiency. One measure of efficiency is the amount of product that is made from a given amount of raw material consumed. Where there is a substantial and varying weight loss from a large volume of water-bearing raw material as it is processed through a plant, it becomes difficult to determine accurately the efficiency of conversion to finished product. The gross weight of the material charged to the plant over a given time period and of the resulting, more or less dehydrated product output may be readily obtained, but such information is only a rough approximation of plant efficiency unless the density and solids content, i.e., the weight of the material charged to plant on a water-free basis, are known.

In making potato chips the yield and color of the fried chips are related to the density of the raw potato feed. For example, the yield may increase by about 22% and the oil content of the chips decrease from 45% to 31%, for an increase in density of the potato feed from 1.06 to 1.09. High density potatoes are, therefore, preferred and require shorter frying time and consume less frying oil. The chips derived from higher density potatoes may also be crisper and stronger. This, the apparatus of the invention could be used to sort or select on a large volume basis, potatoes of higher density for these advantages. Also, one could use the apparatus for selecting potatoes of a narrow density range, and thereby control frying time and chip color more precisely.

With many food materials the initial water content varies due to a number of factors involved such as the materials being derived from a number of sources. For example, the water content of potatoes is usually in the general neighborhood of 80 to 85% and variations in this range can have a marked effect on the properties of the potato chips produced and any determination of plant efficiency. Although one may analyze samples of the raw materials by laboratory techniques to determine their density and solids content this procedure is at best quite unsatisfactory due to problems such as the taking of representative samples, and the large number of analyses that must be made to be of sufficient value. Also, in measuring plant efficiency it is impractical, if not impossible, to run a material balance over the whole plant due to the many processing streams involved and the fact that a large quantity of the water in the raw material may leave the plant as vapor, whose weight is unknown.

In view of these various considerations there is a need for systems capable of determining quickly and accurately on a large scale, the density and solids content of water-bearing food materials that are processed through a commercial plant in a given time period. The present invention provides a system that is particularly suitable for such use and makes it practical to determine by actual, accurate, inexpensive measurement the solids content of most, if not all, of the volume of material that undergoes processing. Moreover, the determination can be accomplished without sample-taking and without the use of laboratory procedures. The present invention utilizes Archimedes' principle that he density and, therefore, the solids content, of a mass of distinct pieces of solid-form, water-bearing materials can be calculated from the determined difference between the weight of a mass or stacked bed of the material in air and the weight when the same material is submerged in water. Archimedes' principle provides that the density of a solid is its weight in air divided by the difference between its weight in air minus its weight in water.

The apparatus of the present invention, although semi-continuous in nature, operates in a manner that resembles a continuous system. The invention is readily adaptable to an essentially automatic operation requiring little operator attention. Heretofore, there have been small scale systems for making density determinations of water-bearing food materials on an essentially laboratory or sampling scale, but to our knowledge no satisfactory equipment is available for measuring the densities and solids contents desired by actual measurement involving virtually the entire volume of material processed in a commercial plant operation.

The measurement of potato density by the use of Archimedes' principle has been used in some laboratories, see *Potato Processing* by Talburt and Smith, pp. 267–269. In one prior device a few pounds of potatoes were weighed in air on a scale from whose beam a basket was suspended on a wire and entirely immersed in water in a vessel having a cut-out section through which displaced water could discharge at a height above the basket. After weighing the potatoes in air with the vessel filled with water, they were placed in the basket in the water, the displaced water was discharged through the cut-out wall section, and the weight again taken. During this measurement the basket was higher in the water than when the measurement was taken in air, but the effect of this difference in immersed weight was limited to the relatively minor difference in the amount of wire submerged at the respective times the separate weights were taken. Although the device was suitable for use on a small scale, it could not be scaled-up readily to handle large volumes of food materials and make accurate density determinations. In contrast, the apparatus of the present invention is quite appropriate for such use and can provide by direct measurement on a virtually continuous basis the density of an entire mass of food material to be processed in a commercial size plant.

The invention can be best understood by describing it in conjunction with the accompanying drawings in which:

FIG. 2 is a control diagram for the apparatus of FIG. 1.

Figure 1:
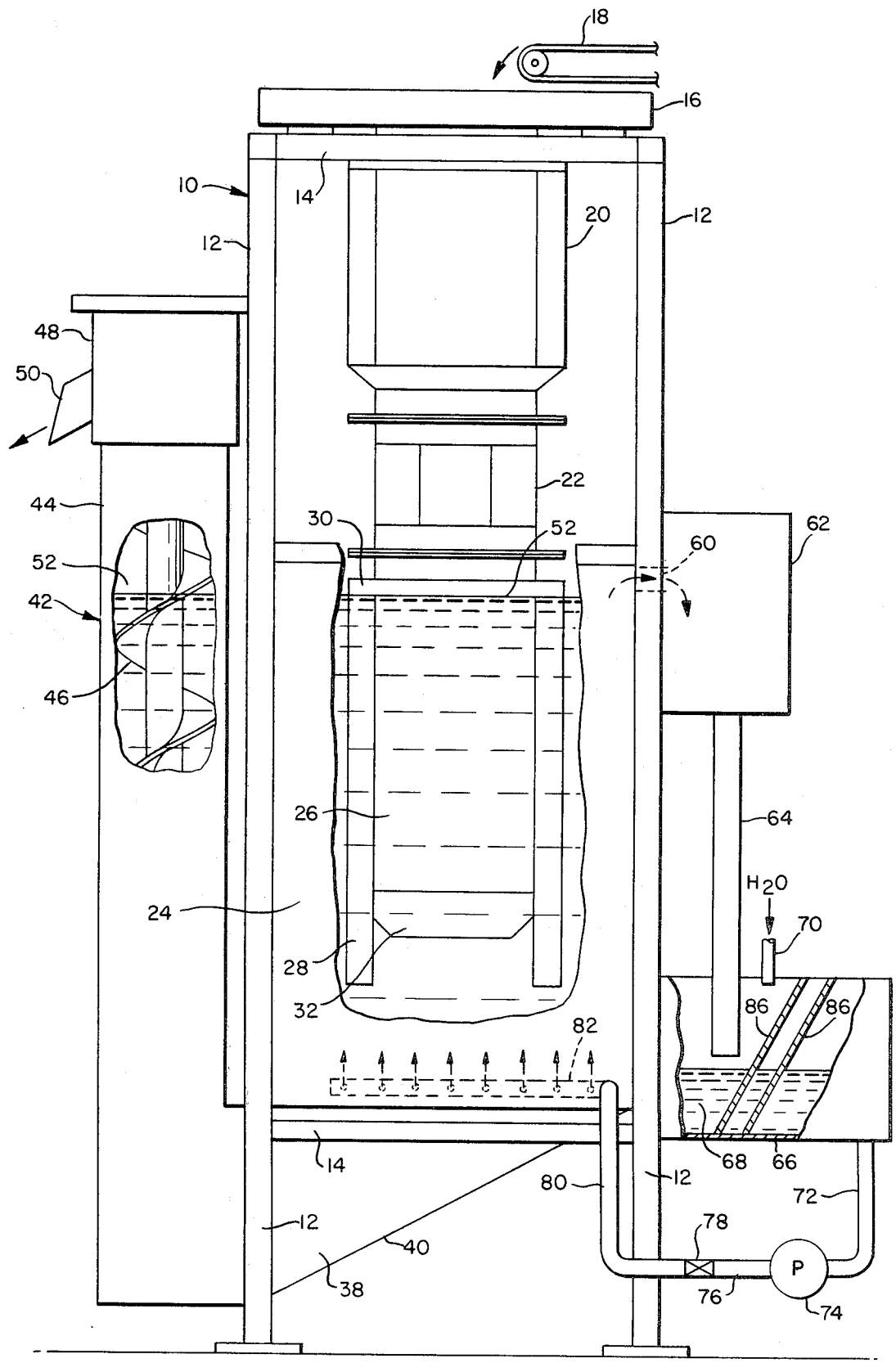
FIG. 1 is a schematic, side view of an apparatus of the invention.

Referring to FIG. 1 there is shown an upstanding open framework 10 having legs 12 on its four corners and cross-pieces 14 for stabilizing the structure. On the top of framework 10 there is positioned a load cell scale 16 of a type known for weighing relatively large masses suspended therefrom with essentially no vertical displacement of the scale during loading. Such movement may, for example, be less than a small fraction of an inch and is, therefore, negligible.

Load cell scale 16 has an open middle area (not shown) through which the free-flow, water-bearing food material in the form of solid pieces can be discharged from an in-feed conveyor 18. The food materials, e.g., farinaceous, essentially solid, particulate food material such as potatoes or corn or other grain, may often be composed of water to a major extent. The pieces of food material drop through the open, middle area of scale 16 into upper hopper or chamber 20 and are contained or held therein as a stationary, settled or fixed bed, by dumper gate 22 in closed position at the lower end of hopper 20. Hopper 20 is suspended in an essentially vertically-fixed position from scale 16. Dumper gate 22 can be actuated between closed and opened positions by an air cylinder or other suitable means (not shown).

The food material is composed of pieces in solid form, and since they have a specific gravity greater than that of water they form a stationary stack or bed in hopper 20 extending to a height depending on the amount of material in a given charge fed by conveyor 18. Thus, conveyor 18 can be actuated to discharge an approximate amount of food material into hopper 22, and when the weight in the hopper increases to the desired amount a control associated with the load cell scale can stop the conveyor. This weight may not be very accurate since as the potatoes drop into hopper 20 the scale may be in a fluctuating state.

The food material charged into hopper 20 forms a stationary bed of particulate material supported on horizontally-disposed elements extending across and closing the passageway through the dumper gate 22. The food material will generally be non-uniformly shaped and forms a fixed bed of solid pieces having interstitial spaces therebetween. The volume of such spaces will depend on factors such as the size and shape of the pieces and their uniformity in shape. These spaces will be filled with gas, most conveniently air, and hopper 20 may have solid or foraminous walls and remains open at the top.

Within the lower part of framework 10 there is positioned a water-filled vessel 24 which has walls and a bottom that are water-tight. Lower chamber 26 extends downwardly from dumper gate 22 and has foraminous side walls held within framing members 28 which may be four or more in number located around chamber 26. Similar supporting members 30 may be disposed around the top of chamber 26. Vessel 24, as well as hopper 20, and lower chamber 26 may be round for maximum strength but could have other cross-sectional shapes. In any event, vessel 24 has an open top and is sufficiently large in volume for receiving lower chamber 26 therein.

Chamber 26 has a dumper gate 32 at the lower end of the chamber, and this gate can also be actuated between open and closed positions by an air cylinder or other suitable means. Lower chamber 26, its supporting members 28 and 30, and dumper gate 32 are all suspended in fixed vertical position from upper dumper gate 22 and, therefore, from scale 16. Chamber 26 is held within vessel 24 but spaced away from the sides of the vessel. Thus, the entire structure formed by hopper 20, lower chamber 26 and dumper gates 22 and 32, along with their attendant supporting structures, is suspended from load cell scale 16 but yet is not subject to vertical movement from the charging of food material into the chambers. Thus, scale 16 is of the type that weighs the suspended structure and anything held therein by dumper gate 22 or 32, without the suspended structure moving vertically within vessel 24 to a significant extent.

The bottom 38 of vessel 24 has a downwardly-inclined lower wall 40 opening into a conveyor that is shown as an auger-type, vertical lift or elevator 42. The elevator has a water-tight, outer tubular wall 44 with an internal auger 46 that extends from the bottom to the top of tube 44 and serves to carry the food materials from the bottom 38 of vessel 24 to the upper part of the elevator 42 where the materials are discharged through trough 50. Auger 46 may be inactivated or stopped during times in which weight measurements are taken, and this insurers the quiescent state of the water in vessel 24.

The apparatus of the invention provides vessel 24 for containing sufficient water to immerse lower chamber 26 to an extent that a charge of the food material when placed in chamber 26 in a stationary, settled manner on dumper gate 32 is also immersed in the water. During operation of the apparatus water is maintained at the same level 52 in vessel 24 and thus in lower chamber 26 and elevator 42.

In operation of the apparatus of the invention, a charge of the food material, after it has been weighed in hopper 20 with lower chamber 26 being empty and the water in vessel 24 at level 52 and in a substantially quiescent state, is dropped by gravity into lower chamber 26 by opening dumper gate 22. At that time, the lower dumper gate 32 is closed and serves to support the charge of food material in chamber 26 as a stationary bed of the material immersed in water having an upper level 52. The water, of course, fills the interstices in the bed between the individual, contacting pieces of food material. Dropping the charge of food material into lower chamber agitates the water therein, and after the water becomes substantially quiescent another weight reading of the total structure suspended from load cell scale 16 is taken with hopper 20 empty and the charge of food material being held in lower chamber 26.

The difference in this weight reading and the weight reading taken when the same charge of food material was held in hopper 20 with the lower chamber 26 being empty can be used to calculate the density and, therefore, the percent of solids in the charge. For example, the weight of 100 pounds of raw potatoes as determined by the first measurement in air may typically weigh on the order of about 7 pounds when immersed in water, the difference in the weights, therefore, being 93 pounds. By handling and weighing in this fashion the entire volume of food material charged to a given plant using the apparatus of the invention, an accurate determination of the amount of fried, or otherwise cooked or dried, product that should be made over a given period of time, e.g., a day, can be determined. The plant is generally controlled so that the product has a substantially constant moisture content, or at least any variation in this respect is relatively insignificant in view of the large amount of water that is removed from the food material during processing, so the amount of moisture in the total product is generally known. For example, in making potato chips from raw potatoes the water content may typically be reduced from about 80% to about 1%. With this formation and the calculation of the density and solids contents for the feed, an accurate determination of plant efficiency may be made.

The apparatus of the invention provides means for maintaining a substantially constant level of water in lower chamber 26. This can readily be done by providing in the upper part of vessel 24 an overflow outlet 60 at the position of water level 52. Thus, when a charge of food material is dumped into lower chamber 26 the resulting displacement of water causes water to overflow through outlet 60 and into upper collecting tank 62. In this manner the water level in vessel 24, lower chamber 26 and conveyor 42 is maintained constant regardless of variations in the volume of food material positioned in chamber 26 at any given time.

The water lost from vessel 24 must be replaced since after a charge of food material is weighed and discharged from lower chamber 26 by way of dumper gate 32 and a generally corresponding volume of the food material is lifted from the water in elevator 42 on the way to being discharged from the apparatus, the water level in vessel 24 would be below overflow outlet 60 even though it may still be above the next charge of food material placed in chamber 26. Unless the water is at level 52 when the next charge of food material is weighed in air and then in water, incorrect weight differences will be determined due to differing amounts of lower chamber 26 and its supporting structure being immersed in the water at the times the separate weights of the discharge are determined in hopper 20 and lower chamber 26, respectively.

To overcome this problem means are provided for supplying water to vessel 24 in a manner in which the water introduced does not agitate the water in vessel 24 to such an extent that a substantially quiescent state cannot be obtained, at least not in a reasonable delay period between the times of taking the separate weight readings on load cell scale 16. In the system shown in FIG. 1, collecting tank 62 is equipped with a conduit 64 extending from the bottom of the tank downwardly into make-up tank 66. The overflow water from outlet 60 thus drops through conduit 64 into tank 66. A suitable level of water 68 can be maintained in tank 66 by a simple float mechanism (not shown) which controls the addition of make-up water through line 70.

Water leaves the bottom of tank 66 by way of conduit 72 which is an inlet line for centrifugal pump 74. The pump can be run intermittently and be actuated whenever the water level in tank 24 is below the overflow outlet 60. The pump can thus be inactivated or stopped when weight readings are taken to insure that the water in vessel 24 is relatively quiescent. Water is discharged from pump 74 through line 76, check valve 78 which prevents backflow when the pump is stopped, line 80 leading into the lower part of vessel 24, and sparger tube 82. The sparger tube is of a length such that the flow of water into vessel 24 is distributed through a sufficient number of inlet holes along the sparger tube not to agitate the water in vessel 24 to such an extent that an appropriately accurate weight reading cannot be obtained by load cell scale 16 during the time alotted.

Also during the recycling of water by way of tanks 62 and 66, the water can be treated in any suitable manner advisable. For example, in the case of potatoes, which may be peeled or unpeeled when weighed, small pieces of potato or peel may find their way into the water. These solids may be removed by filtering the water as it passes through tank 66, and FIG. 1 shows filters 86 positioned in the flow path between lines 64 and 72 for this purpose.

Rather than provide a water recycle system, the overflow water can simply be discarded or used in another operation of the plan. In this situation make-up water could be supplied to pump 74 from any suitable source.

Although the construction and operation of an apparatus of the invention are apparent from the foregoing description, the system can be further explained by referring to the control or timing diagram of FIG. 2. In FIG. 2, the course of a given charge of material is considered as it passes through the apparatus. At the start of an operation hopper 20 and lower chamber 26 are empty and their respective dumper gates are closed with all equipment being stopped. Vessel 24 has been filled with water to the level of overfow outlet 60. These conditions are indicated by box 102 in FIG. 2. The conveyor 18 is then actuated to load potatoes into hopper 20 per box 104. As long as a preset weight 106 is not met the operation of conveyor 18 continues as shown by line 108.

When the preset weight is met by loading the potatoes in hopper 20 as indicated by line 110, the conveyor 18 is stopped as shown at 112. The weight in load scale 16 is taken per 114 to indicate the dry weight of the potatoes loaded into hopper 20. This dry weight of the potatoes is stored at 116.

Dumper gate 22 is then opened as shown at 118 to drop the load of potatoes into submerged chamber 26. Gate 22 can then be closed. This condition is indicated at 120. After the water in vessel is sufficiently quiescent or stable, another weight is taken by load cell 16 as shown at 122, and this submerged weight of the potatoes is stored at 124. The difference between these determined dry and submerged weights can be used to calculate the density of the involved potatoes.

After the submerged weight of the potatoes is taken, exit conveyor 46 can be started as indicated at 126 in FIG. 2. The lower gate 32 is opened at 128 to dump the potatoes from chamber 26, and then the gate is closed. As potatoes are removed from the water by conveyor 46 the level of water goes below overflow outlet 60. After the potatoes are removed conveyor 46 is stopped. The conveyor runs a sufficient length of time to remove enough potatoes so that the next batch that is weighed in chamber 26 can be freely dumped. Pump 74 is actuated to fill the tank 24 to the level of outlet 24 after conveyor 46 is stopped. The operation of conveyor 46 and pump 74 need not be entirely sequential. Pump 74 is then stopped and the loading, weight measuring, unloading and removal cycle can be repeated more or less continuously or intermittently as desired.

It is claimed:

1. An apparatus suitable for use in weighing freeflowing, solid, particulate, food material having water therein comprising scale means, a first chamber for containing said food material in fixed position, a second chamber for containing said food material in fixed position, means for charging said food material to one of said chambers, passage means for passage of said food material between said first and second chambers, said first and second chambers and said passage means being suspended in essentially fixed, vertical position from said scale means, vessel means in which one of said chambers is positioned, said chamber in said vessel being foraminous, said vessel being suitable for containing water in a substantially quiescent state at a level of water sufficient for submerging said food material in said water in said foraminous chamber, means for maintaining a substantially constant level of water in said vessel, said scale means being suitable for weighing said first and second chambers and said passage means with said level of water being maintained and with a given charge of said food material in one of said chambers and for weighing said first and second chambers and said passage means with said level of water being maintained and said charge of said food material being in the other of said chambers submerged in said water, means for discharging food material from said foraminous chamber, and means for discharging food material from said apparatus after said weight determinations with said food material in said chambers has been made.

2. The apparatus of claim 1 in which there is provided conveyor means for discharging said food material from said vessel, said conveyor means being in fluid communication with said vessel and being suitable for maintaining water therein at said level for water in said vessel.

3. The apparatus of claim 1 or 2 in which there is provided water overflow means in said vessel at said level at which water may be maintained therein.

4. The apparatus of claim 3 in which there is provided means for returning to said vessel water discharged through said water overflow means.

5. This apparatus of claim 4 in which said water return means includes a pump and an inlet in the lower portion of said vessel.

6. An apparatus suitable for use in weighing free-flowing, solid, particulate food material having water therein comprising scale means, an upper chamber suspended in essentially fixed, vertical position from said scale means and being suitable for holding said food material, a vessel below said upper chamber, a foraminous lower chamber in said vessel and suspended in essentially fixed, vertical position from said upper chamber, said lower chamber being positioned to receive a charge of said food material passed by gravity from said upper chamber, means for feeding a charge of food material into said upper chamber for holding a charge of said food material as a stationary settled bed in said upper vessel, means for passing said charge of food material by gravity from said upper chamber to said lower chamber, said vessel being suitable for holding water substantially quiescent at a given level in said lower chamber and said vessel, means for holding said charge of food material as a stationary, settled bed in said lower chamber below said level of water, means for maintaining said water level in said lower chamber and said vessel, means for discharging said charge of food material from said lower chamber into said vessel, said scale means being suitable for weighing in sequence a said charge of food material in said upper chamber with said lower chamber having no food material therein, and then weighing said charge of food material in said lower chamber with there being no food material in said upper chamber, and conveyor means in fluid communication with the lower portion of said vessel and extending upwardly above the height at which said level of water may be maintained in said vessel and lower chamber for removing from said vessel food material discharged from said lower chamber after said weighings have been made.

7. The apparatus of claim 6 in which there is provided water overflow means in said vessel at said level at which water may be maintained therein.

8. The apparatus of claim 7 in which there is provided means for returning to said vessel water discharged through said water overflow means.

9. The apparatus of claim 8 in which said water return means includes a pump and air inlet in the lower portion of said vessel.

10. An apparatus suitable for use in weighing free-flowing, solid, particulate food material having water therein comprising a frame, scale means supported on an upper part of said frame, an upper chamber suspended in essentially fixed, vertical position from said scale means and being suitable for holding said food material, a vessel in a lower part of said frame for holding a volume of water, a foraminous lower chamber in said vessel and suspended in essentially fixed, vertical position from said upper chamber, said lower chamber being positioned to receive a charge of said food material passed by gravity from said upper chamber, conveyor means for feeding a charge of food material into said upper chamber, means for holding a charge of said food material as a stationary, settled bed in said upper chamber, means for passing said charge of food material by gravity from said upper chamber to said lower chamber, said vessel being suitable for holding water substantially quiescent at a given level in said lower chamber, means for holding said charge of food material as a stationary, settled bed in said lower chamber below said level of water, means for discharging said charge of food material from said lower chamber into said vessel, said scale means being suitable for weighing in sequence a said charge of food material in said upper chamber with said lower chamber having no food material therein, and then weighing said charge of food material in said lower chamber with there being no food material in said upper chamber, water-tight conveyor means in fluid communication with the lower portion of said vessel and extending upwardly above the height at which said level of water may be maintained in said vessel and lower chamber for removing from said vessel food material discharged from said lower chamber after said weighings have been made.

11. The apparatus of claim 10 in which there is provided water overflow means in said vessel at said level at which water may be maintained therein.

12. The apparatus of claim 10 or 11 in which there is provided pump means for charging water to the lower portion of said vessel.

13. The apparatus of claim 12 in which there is provided means for stopping said conveyor means and said pump means when said weighings are made by said scale means.

* * * * *

UNITED STATES PATENT AND TRADEMARK OFFICE
CERTIFICATE OF CORRECTION

PATENT NO. : 4,320,658
DATED : March 23, 1982
INVENTOR(S) : Hilton, et al.

It is certified that error appears in the above-identified patent and that said Letters Patent is hereby corrected as shown below:

Column 1, line 42, "This" should be --Thus--.

Column 2, line 11, "he" should be --the--.

Column 5, line 29, "discharge" should be --charge--.

Signed and Sealed this

Sixth Day of December 1983

[SEAL]

Attest:

GERALD J. MOSSINGHOFF

Attesting Officer    Commissioner of Patents and Trademarks